United States Patent [19]

Paciorek et al.

[11] 4,281,185

[45] Jul. 28, 1981

[54] SYMMETRICAL DIPHOSPHATETRAAZACYCLOOCTATETRAENES

[75] Inventors: Kazimiera J. L. Paciorek, Corona Del Mar; Reinhold H. Kratzer, Irvine; Thomas I. Ito, Fountain Valley; James H. Nakahara, Irvine, all of Calif.

[73] Assignee: The United States of America as represented by the Secretary of the Air Force, Washington, D.C.

[21] Appl. No.: 163,134

[22] Filed: Jun. 26, 1980

[51] Int. Cl.³ .......................... C07F 9/22; C10M 1/44
[52] U.S. Cl. .................................. 564/13; 252/49.9; 252/389 A; 252/400 A
[58] Field of Search ............ 564/13; 252/49.9, 389 A, 252/400 A

[56] References Cited

U.S. PATENT DOCUMENTS

| | | |
|---|---|---|
| 3,304,270 | 2/1967 | Dickerson ................................ 260/2 |
| 3,463,813 | 8/1969 | Dickerson ............................. 564/13 |
| 3,711,542 | 1/1973 | Hook et al. ............................ 564/13 |
| 3,846,374 | 11/1974 | Farley et al. .......................... 564/13 |
| 4,166,071 | 8/1979 | Paciorek et al. ...................... 564/13 |
| 4,215,072 | 7/1980 | Paciorek et al. ................ 252/49.9 X |

OTHER PUBLICATIONS

Zhur. Obshch. Khim., vol. 32, No. 9, (1962).

*Primary Examiner*—Thomas A. Waltz
*Attorney, Agent, or Firm*—Donald J. Singer; William J. O'Brien

[57] ABSTRACT

A method for synthesizing symmetrical diphosphatetraazacyclooctatetraenes and the products produced thereby. The synthesis involves effecting a reaction between a diaryltrihalophosphorane of a perfluoroalkyl amidine in the presence of an acid acceptor.

8 Claims, No Drawings

SYMMETRICAL DIPHOSPHATETRAAZACYCLOOCTATETRAENES

STATEMENT OF GOVERNMENT INTEREST

The invention described herein may be manufactured and used by or for the Government for governmental purposes without the payment of any royalty thereon.

BACKGROUND OF THE INVENTION

This invention relates to the synthesis of symmetrical diphosphatetraazacyclooctatetraenes and to novel eight-membered ring heterocyclic compounds produced thereby. More particularly, this invention concerns itself with a novel method for synthesizing 1,5-diphospha-2,4,6,8-tetraazacyclooctatetraenes. The resulting products exhibit excellent antioxidant and anticorrosion characteristics making them excellent candidates for use as additives in engine oils, hydraulic fluids and greases as well as in other applications apparent to those skilled in the art.

Present interest in the utilization of perfluorinated fluids for high temperature lubricant applications has provided an impetus in a research effort directed toward the discovery of antioxidant and anticorrosive additives. Because of their thermal stability, the perfluorinated fluids have a great potential for use in lubrication and hydraulic applications. However, there is a serious drawback in their use resulting from the fact that certain metals present in aircraft components tend to corrode and degrade the fluids being used as lubricants. This occurs at temperatures above 550° F. in an oxidative environment.

It would be highly desirable, therefore, to provide an additive for the perfluorinated fluids that would overcome the degradation and corrosion problems associated with their use. As a consequence, a considerable research effort has evolved in an attempt to provide such additives and an efficient and convenient method for their synthesis. As a result of this effort, it has been found that symmetrical diphosphatetraazacyclooctatetraenes can be obtained by effecting a reaction between a perfluoroalkylether amidine and a trihalophosphorane. The corrosion problems encountered when using perfluorinated fluid lubricants are obviated by using the additives of this invention.

SUMMARY OF THE INVENTION

In accordance with this invention, it has been found that symmetrical diphosphatetraazacyclooctatetraenes can be prepared by effecting a reaction between a perfluorinated amidine and a diaryltrihalophosphorane in the presence of an acid acceptor at temperatures ranging from about 30° to 100° C. The resulting 8-membered ring heterocyclic compounds are illustrated by the following structural formula

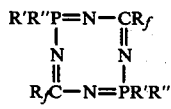

wherein R' and R" substituents on the phosphorus can be the same or different and are selected from the group consisting of aryl radicals such as $C_6H_5$ and $R$—$C_6H_4$, and perfluoroaryl radicals such as $C_6F_5$ and $R_fC_6F_4$; R is selected from the group consisting of aryl, alkyl, perfluoroalkyl and perfluoroalkylether radicals; $R_f$ is selected from perfluoroalkyl and perfluoroalkylether radicals as represented by the general formula $C_nF_{2n+1}$, $C_2F_5(OCF_2CF_2)_nOCF_2$, $C_3F_7[OCF(CF_3)CF_2]_nOCF(CF_3)$, or any combinations thereof which are readily apparent to those skilled in the art. The letter n represents an integer of from zero to 20.

Accordingly, the primary object of this invention is to provide a convenient and efficient method for synthesizing symmetrical diphosphatetraazacyclooctatetraenes.

Another object of this invention is to provide a novel series of compounds which are especially useful as antioxidant and anticorrosive additives for perfluorinated lubricants.

Still another object of this invention is to provide a convenient process for synthesizing symmetrical cyclooctatetraenes through the interreaction of a perfluoroalkylether amidine and a trihalophosphorane.

The above and still further objects and advantages of the present invention will become more readily apparent upon consideration of the following detailed disclosure thereof.

DESCRIPTION OF THE PREFERRED EMBODIMENT

The present invention encompasses a process for synthesizing symmetrical diphosphatetraazacyclooctatetraenes by reacting perfluoroalkyl or perfluoroalkylether amidine with a diaryltrihalophosphorane. The resulting 8-membered ring heterocyclic compounds possess great potential as antioxidant and anticorrosive additives for use in perfluorinated fluid lubricants, greases and hydraulic fluids. They are best illustrated by the following general structure:

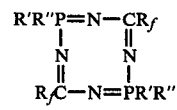

while the procedure for synthesizing these compounds can best be exemplified by referring to the following general equation:

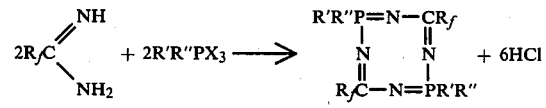

wherein the diaryltrihalophosphorane is reacted with an equimolar quantity of perfluoroalkylether or perfluoroalkyl amidine at 30° to 100° C. in the presence of an acid acceptor giving concurrently with hydrogen halide elimination a symmetrical diphosphatetraazacyclooctatetraene. The substituent $R_f$ can be selected from perfluoroalkyl and perfluoroalkylether groups as represented by the general formulae $C_nF_{2n+1}$, $C_2F_5(OCF_2CF_2)_nOCF_2$, or $C_3F_7[OCF(CF_3)CF_2]_nOCF(CF_3)$. The substituents R' and R" on the phosphorus can be the same or different aryl groups such as $C_6H_5$, $R$—$C_6H_4$ (wherein R can be aryl, alkyl, perfluoroalkyl or a perfluoroalkylether moiety), perfluoroaryl ($C_6F_5$, $R_fC_6F_4$), or any other type of a substituent as should be readily apparent to those skilled in the art. The substituent X on the phosphorus can be either chlorine or bromine. The letter n is an integer of from zero to 20.

The materials to be used in preparing the 1,5-diphospha-2,4,6,8-tetraazacyclooctatetraene are known compounds that are described in the literature. Diphenyltrichlorophosphorane is a common chemical, whereas perfluoroalkylether amidines are described by P. D. Schuman et al in British Pat. No. 1,350,806 (1974).

The following examples are presented in order to more fully understand the nature of the invention and how it may be carried into effect. These examples illustrate specific embodiments of the invention and are not to be construed as limiting the invention in any way.

EXAMPLE I

Under nitrogen by-pass, a solution of amidine, $C_3F_7OCF(CF_3)C(=NH)NH_2$, (2.89 g, 8.81 mmol) and triethylamine (3.9 ml, 27.96 mmol) in Freon-113 (20 ml) was added over a period of 1.7 hr to a solution of diphenyltrichlorophosphorane (5.48 g, 18.8 mmol) in benzene (50 ml) at 50° C. The mixture was then stirred at 50° C. for 87 hr. After removal of solvents under reduced pressure, the residue was treated with Freon-113 (5×15 ml) and filtered through a 1.5×5 cm column of Woelm neutral alumina. The product (2.17 g, 47% yield) was distilled in vacuo giving the desired 1,5-bis(-diphenylphospha)-3,7-bis[$C_3F_7OCF(CF_3)$]-2,4,6,8-tetraazacyclooctatetraene (1.46 g, 31.5%); bp 138°–139° C./0.001 mm Hg; mp 77.5°–79° C.

Anal. Calcd. for $C_{36}H_{20}F_{22}N_4O_2P_2$: C, 42.37; H, 1.98; F, 40.96; N, 5.49; P, 6.07; O, 3.14; MW, 1020.49. Found: C, 42.56; H, 2.03; F, 41.14; N, 5.53; P, 5.42; MW, 1130.

The product of Example I is illustrated by the following structural formula

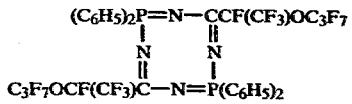

The above 1,5-bis(diphenylphospha)-3,7-bis [$C_3F_7OCF(CF_3)$]-2,4,6,8-tetraazacyclooctatetraene was found to effectively inhibit oxidation of perfluoroalkylether fluids, e.g., fluids of the type disclosed in U.S. Pat. No. 3,393,151 and to prevent corrosion of various metals by these fluids. For example, a 1% by weight solution of this diphosphatetraazacyclooctatetraene decreased oxygen consumption to zero and volatile products formation by a factor of ~17 during a 24 hour exposure to oxygen at 600° F. as compared to an identical treatment of the fluid in the absence of the additive. In addition, an M-50 coupon test surface in the presence of the additive appeared unchanged, whereas in the absence of any additive, under otherwise identical conditions, the surface becomes covered with deeply colored irregular deposits. These data are summarized below in Table I.

TABLE I

Degradation of Krytox 143 AC Fluid
(a product of E.I. du Pont de Nemours and Co.)
in the Presence of M-50 Alloy Coupon at
600° F. in Oxygen for 24 hr[a]

| Fluid Used g | Additive | Oxygen Consumed Total mg | %[b] | mg/g[c] | Total Products Formed mg | mg/g[d] |
|---|---|---|---|---|---|---|
| 12.13 | none | 70.8 | 24.6 | 5.84 | 576.7 | 47.54 |
| 12.16 | 1%[e]$C_{36}H_{20}F_{22}N_4O_2P_2$ | 0.0 | 0.0 | 0.0 | 34.9 | 2.87 |

[a]The apparatus consisted of a sealed glass tube wherein the metal coupon was suspended in the fluid; the test was conducted in pure oxygen; at the conclusion of the test, the oxygen was measured and the products were collected and measured.
[b]Percent of oxygen available.
[c]Oxygen consumed in mg/g Krytox employed.
[d]Products formed in mg/g Krytox employed.
[e]The percent is weight percent of additive per weight of Krytox fluid.

EXAMPLE II

Under nitrogen by-pass, a solution of the amidine, $C_3F_7OCF(CF_3)CF_2OCF(CF_3)C(=NH)NH_2$, (3.14 g, 6.36 mmol) and triethylamine (5.4 ml, 38.72 mmol) in Freon-113 (25 ml) was added dropwise over 28 min. to a solution of diphenyltrichlorophosphorane (3.86 g, 13.24 mmol) in benzene (25 ml) at 50° C. The resulting mixture was stirred at 50° C. for 114 hr. After cooling, Freon-113 (75 ml) was added and the insoluble portion was removed by filtration. The concentrated filtrate was then refiltered through a 1.5×5 cm column of Woelm neutral alumina giving 1,5-bis(diphenylphospha)-3,7-bis[$C_3F_7OCF(CF_3)CF_2OCF(CF_3)$]-2,4,6,8-tetraazacyclooctatetraene as a viscous fluid.

Anal. Calcd. for $C_{42}H_{20}F_{34}N_4O_4P_2$: C, 37.30; H, 1.49; F, 47.76; N, 4.14; P, 4.58; O, 4.73; MW, 1352.55. Found: C, 38.04; H, 1.55; F, 47.77; N, 4.04; P, 4.52; MW, 1200.

The product of Example II is illustrated by the following structural formula:

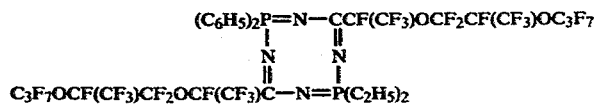

While the invention has been described with particularity in reference to specific embodiments thereof, it is to be understood that the disclosure is for the purpose of illustration only and that various modifications and alterations may be made without departing from the spirit of the invention, the scope of which is defined by the appended claims.

What is claimed is:

1. A process for synthesizing symmetrical diphosphatetraazacyclooctatetraenes which comprises the steps of (1) forming a reaction mixture composed of (a) a diaryltrihalophosphorane and (b) a perfluorinated amidine; (2) heating said reaction mixture in the presence of an acid acceptor for a period of time and at a temperature sufficient to effect a reaction therebetween; and (3) separating the resulting reaction product.

2. A process in accordance with claim 1 wherein said diaryltrihalophosphorane is diphenyltrichlorophosphorane.

3. A process in accordance with claim 1 wherein said amidine is $C_3F_7OCF(CF_3)C(=NH)NH_2$.

4. A process in accordance with claim 1 wherein said amidine is C₃F₇OCF(CF₃)CF₂OCF(CF₃)C(=NH)NH₂.

5. A process in accordance with claim 1 wherein said acid acceptor is triethylamine and said reaction mixture is heated to a temperature of from about 30° to 100° C.

6. A process in accordance with claim 1 wherein the components of said reaction mixture are present in equimolar proportions.

7. The compound 1,5-bis(diphenylphospha)-3,7-bis[C₃F₇OCF(CF₃)]-2,4,6,8-tetraazacyclooctatetraene.

8. The compound 1,5-bis(diphenylphospha)-3,7-bis[C₃F₇OCF(CF₃)CF₂OCF(CF₃)]-2,4,6,8-tetraazacyclooctatetraene.

* * * * *